US006773926B1

(12) United States Patent
Freund et al.

(10) Patent No.: US 6,773,926 B1
(45) Date of Patent: Aug. 10, 2004

(54) NANOPARTICLE-BASED SENSORS FOR DETECTING ANALYTES IN FLUIDS

(75) Inventors: Michael S. Freund, Sierra Madre, CA (US); Nathan S. Lewis, La Canada, CA (US); Shawn M. Briglin, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 394 days.

(21) Appl. No.: 09/963,788

(22) Filed: Sep. 25, 2001

Related U.S. Application Data (60) Provisional application No. 60/235,380, filed on Sep. 25, 2000.

(51) Int. Cl.$^7$ ................................................. G01N 27/00
(52) U.S. Cl. ...................... 436/149; 436/151; 436/119; 436/120; 436/111; 436/73; 436/80
(58) Field of Search ................................ 436/149, 151, 436/183, 119, 120, 111, 73, 80

(56) References Cited

U.S. PATENT DOCUMENTS

| | | |
|---|---|---|
| 3,927,930 A | 12/1975 | Goldberg et al. |
| 4,453,126 A | 6/1984 | Volgyesi |
| 4,644,101 A | 2/1987 | Jin et al. |
| 4,737,112 A | 4/1988 | Jin et al. |
| 4,923,739 A | 5/1990 | Jin et al. |
| 4,980,541 A | 12/1990 | Shafer et al. |
| 5,104,210 A | 4/1992 | Tokas et al. |
| 5,298,783 A | 3/1994 | Wu |
| 5,429,975 A | 7/1995 | Sheu et al. |
| 5,451,920 A | 9/1995 | Hoffheins et al. |
| 5,512,882 A | 4/1996 | Stetter et al. |
| 5,571,401 A | * 11/1996 | Lewis et al. ................. 205/787 |
| 5,677,662 A | 10/1997 | Bresolin et al. |
| 5,698,771 A | 12/1997 | Shields et al. |
| 5,742,223 A | 4/1998 | Simendinger et al. |
| 5,922,537 A | 7/1999 | Ewart et al. |
| 5,942,674 A | 8/1999 | Logothetis et al. |
| 6,002,817 A | 12/1999 | Kopelman et al. |
| 6,202,471 B1 | 3/2001 | Yadav et al. |
| 6,221,673 B1 | 4/2001 | Snow et al. ................. 436/149 |
| 2003/0109056 A1 | * 6/2003 | Vossmeyer et al. .......... 436/169 |

FOREIGN PATENT DOCUMENTS

| | | | | |
|---|---|---|---|---|
| EP | 1120648 A1 | * | 8/2001 | .......... G01N/31/00 |
| JP | 2000266753 A | * | 9/2000 | .......... G01N/33/68 |
| WO | WO 99/21934 | * | 5/1999 | |
| WO | 99/273557 | | 6/1999 | |
| WO | WO 00/14520 | * | 3/2000 | |

OTHER PUBLICATIONS

Scott et al. "Laser Desorption FT–MS Exchange Studies of Air–Oxidized Alkanethiol Self–Assembled Monolayers on Gold", Ana Chem., 1997, v. 69, pp. 2636–2639.*

Wohltjen et al. "Colloidal Metal–Insulator–Metal Ensemble Chemiresistor Sensor", Anal. Chem., 1998, v. 70, No. 14, pp. 2856–2859.*

Brust, et al., "Synthesis of Thiol–derivatised Gold Nanoparticles in a Two–phase Liquid–Liquid System", *J. Chem. Soc. Chem. Commun.*, No. 7, pp. 801–802, Apr., 1994.

(List continued on next page.)

*Primary Examiner*—Yelena G. Gakh
(74) *Attorney, Agent, or Firm*—Fish & Richardson P.C.

(57) ABSTRACT

Sensors, sensor arrays and sensing methods provide for detection of a chemical analyte in a fluid. Sensors include a plurality of conductive and nonconductive regions in contact with a measuring apparatus. One or more sensors include a plurality of particles that include a metallic core. Preferably, the particles also include one or more capping ligands coupled to the metallic core. Exposure of the sensors to a fluid containing a chemical analyte causes the analyte to react with the metal core, preferably by displacing one or more of the capping ligands. The chemical analyte can be detected based on a change in electrical or optical properties of the sensors.

21 Claims, 9 Drawing Sheets-

OTHER PUBLICATIONS

Elghanian, et al., "Selective Colorimetric Detection of Polynucleotides Based on the Distance–Dependent Optical Properties of Gold Nanoparticles", *Science*, vol. 277, pp. 1078–1081, Aug., 1997.

Green et al., "Three–Dimensional Monolayers: Nanometer–Sized Electrodes of Alkanethiolate–Stabilized Gold Cluster Molecules", J. Phys. Chem. B, vol. 101, pp. 2663–2668 (1997).

Henglein, Arnim, "Physicochemical Properties of Small Metal Particles in Solution: "Microelectrode" Reactions, Chemisorption, Composite Metal Particles, and the Atom–to–Metal Transition", *J. of Phys. Chem*, vol. 97, No. 21, pp. 5457–5471, Feb., 1993.

Hostetler, et al., "Alkanethiolate Gold Cluster Molecules with Core Diameters from 1.5 to 5.2 nm: Core and Monolayer Properties as a Function of Core Size", *Langmuir*, vol. 14, pp. 17–30 (1998).

Hostetler, et al., "Monolayers in Three Dimensions: Synthesis and Electrochemistry of –ω–functionalized Alkanethiolate–Stabilized Gold Cluster Compounds", *J. Am. Chem. Soc.*, vol. 118, No. 17, pp. 4212–4213, May, 1996.

Ingram, et al., "Poly–hetero–ω–functionalized Alkanethiolate–Stabilized Gold Cluster Compounds", *J. Am. Chem. Soc.*, vol. 119, No. 39, pp. 9175–9178, Oct., 1997.

Lee, et al., "Electron Hopping and Electronic Conductivity in Monolayers of Alkanethiol–Stabilized Gold Nano–Clusters at the Air/Water Interface", *Israel Journal of Chemistry*, vol. 37, Nos. 2–3, pp. 213–223, Jul., 1997.

Leff, et al. "Synthesis and Characterization of Hydrophobic, Organically–Soluble Gold Nanocrystals Functionalized with Primary Amines", *Langmuir*, 12, pp. 4723–4730 (1996).

Leff et al., "Thermodynamic Control of Gold Nanocrystal Size: Experiment and Theory", J. Phys. Chem., vol. 99, pp. 7036–7041 (1995).

Templeton, et al., "Reactivity of Monolayer–Protected Gold Cluster Molecules: Steric Effects", *J. Am. Chem. Soc.,* 120, pp. 1906–1911 (1998).

Zeiri, et al., Studies of Silver Organosois: Preparation, Characterization, and Cyanide–Induced Aggregation, *J. Phys. Chem.*, vol. 96, No. 14, pp. 5908–5917, Jul., 1992.

Longergan, et al.., "Array–Based Vapor Sensing Using Chemically Sensitive, Carbon Black–Polymer Resistors", *Chem. Mater.*, vol. 8, pp. 2298–2312, 1996.

Luedtke, et et al., "Strucutre, Dynamics, and Thermodynamics of Passivated Gold Nanocrystallites and Their Assemblies", *The Journal of Physical Chemistry*, vol. 100, No. 32, pp. 13323–13329, Aug. 8, 1996.

Snow, et al., "Size–Induced Metal to Semiconductor Transition in a Stabilized Gold Cluster Ensemble", *Chemistry of Materials*, vol. 10, No. 4, pp. 947–949, Apr., 1998.

Terrill, et al., "Monolayers in Three Dimensions: NMR, SAXS, Thermal, and Electron Hopping Studies of Alkanethol Stabilized Gold Clusters", *J. Am. Chem. Soc.*, vol. 117, pp. 12357–12548, 1995.

Wohltjen, et al., "Colloidal Metal–Insulator–Metal Ensemble Chemiresistor Sensor", *Analytical Chemistry*, vol. 70, No. 14, pp. 2856–2859, 1998.

Zeiri, et al., "Studies of Silver Organosols: Preparation, Characterization, and Cyanide–Induced Aggregation", *J. Phys. Chem.*, vol. 96, pp. 5908–5917, 1992.

Grate, et al., "Role of Selective Sorption in Chemiresistor Sensors for Organophosphorus Detection", *Analytical Chemistry*, vol. 62, pp. 1927–1934, Sep. 1990.

* cited by examiner

NANOPARTICLE-BASED SENSORS FOR DETECTING ANALYTES IN FLUIDS

CROSS-REFERENCE TO RELATED APPLICATION

This application claims the benefit of Provisional Application No. 60/235,380, filed on Sep. 25, 2000, which is incorporated by reference herein.

FEDERALLY SPONSORED RESEARCH OR DEVELOPMENT

The U.S. Government may have certain rights in this invention pursuant to Grant No. DAAK60-97-K-9503 awarded by DARPA.

TECHNICAL FIELD

This invention relates generally to sensors and sensor systems for detecting analytes in fluids and, more particularly, to sensor systems that incorporate sensors having electrical properties that vary according to the presence and concentration of analytes, and to methods of using such sensor systems.

BACKGROUND

There is considerable interest in developing sensors that act as analogs of the mammalian olfactory system (Lundstrom et al., Nature 1991, 352, 47–50; Shurmer et al., Sens. Act. B 1992, 8, 1–11; Shurmer et al., Sens. Actuators B 1993, 15, 32). Prior attempts to produce broadly responsive sensors and enhanced sensor arrays have exploited heated metal oxide thin film resistors (Gardner et al., Sens. Act. B 1991, 4, 117–121; Gardner et al., Sens. Act. B 1991, 6, 71–75), polymer sorption layers on the surfaces of acoustic wave (SAW) resonators (Grate et al., Sens. Act. B 1991, 3, 85–111; Grate et al., Anal. Chem. 1993, 65, 1868–1881), arrays of electrochemical detectors (Stetter et al., (1986) Anal. Chem. 1986, 58, 860–866; Stetter et al., Sens. Act. B 1990, 1, 43–47; Stetter et al., Anal. Chem. Acta 1993, 284, 1–11), conductive polymers or composites that consist of regions of conductors and regions of insulating organic materials (Pearce et al., Analyst 1993, 118, 371–377; Shurmer et al., Sens. Act. B 1991, 4, 29–33; Doleman et al., Anal. Chem. 1998, 70, 2560–2654; Lonergan et al., Chem. Mater. 1996, 8, 2298). Arrays of metal oxide thin film resistors, typically based on tin oxide ($SnO_2$) films that have been coated with various catalysts, yield distinct, diagnostic responses for several vapors (Corcoran et al., Sens. Act. B 1993, 15, 32–37). Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHZ Rayleigh wave in the crystal. Attempts have also been made to construct arrays of sensors with conducting organic polymer elements that have been grown electrochemically through use of nominally identical polymer films and coatings. Moreover, Pearce et al., Analyst 1993, 118, 371–377, and Gardner et al., Sens. Act. B 1994, 18–19, 240–43 describe, polypyrrole based sensor arrays for monitoring beer flavor. U.S. Pat. No. 4,907,441, describes general sensor arrays with particular electrical circuitry. U.S. Pat. No. 4,674,320 describes a single chemoresistive sensor having a semi-conductive material selected from the group consisting of phthalocyanine, halogenated phthalocyanine and sulfonated phthalocyanine, which was used to detect a gas contaminant. Other gas sensors have been described by Dogan et al., Synth. Met. 1993, 60, 27–30, and Kukla, et al., Films. Sens. Act. B., Chemical 1996, 37, 135–140. Each of the above-cited references is incorporated by reference herein.

Volatile sulfur compounds stand out in that humans are far more sensitive to these vapors than to analogous alcohols, alkanes, ketones, or esters, for example. Humans have odor detection thresholds for volatile sulfur compounds in the part per billion (ppb) range. Thiols are consumed in many foods and the liver is responsible for eliminating them from the body. Reports have shown elevated levels of several volatile sulfur compounds in the lung air of patients with various disease states. An electronic nose with high sensitivity for thiols could thus sense and discriminate these molecules, potentially providing a simple method for diagnosis of these diseases.

However, an electronic nose formed from composites conductors and insulating organic materials does not display the enhanced sensitivity to thiols, relative to analogous alcohols or ketones for example, that humans possess. A similar phenomenon occurs for biogenic amines, where humans have enhanced sensitivity relative to that displayed from sensors that use arrays of composites formed from regions of conductors and regions of insulating organic material. Thus, there remains a need for sensors having enhanced sensitivity for thiols and other organic compounds.

SUMMARY

The invention provides sensing apparatus, including sensors and sensor arrays, and methods for detecting a chemical analyte, in particular a thiol-containing analyte, in a fluid.

In general, in one aspect, the invention provides sensors, sensor arrays and sensing methods implementing techniques for detecting chemical analytes in fluids. One or more sensors are provided, which include regions of conductive material and regions of nonconductive material proximate to the conductive material. The nonconductive material includes a chemical group coupled to the conductive material. The chemical group is displaceable by a chemical analyte. The sensors are exposed to a fluid containing the chemical analyte under conditions sufficient to cause the chemical analyte to displace the chemical group. A response is measured based on the displacement of the chemical group. The chemical analyte is detected based on the measured response.

Particular implementations may include one or more of the following features. The conductive material can include a plurality of particles, which can include one or more metals or metal alloys. The particles can include a metal core. The chemical group can be a ligand covalently coupled to the metal core. In a preferred embodiment, the chemical analyte is a thiol, the metal core includes gold or silver, and the chemical group is an alkylamine. The particles can be disposed in a polymer matrix, which can include a conducting, semiconducting, or insulating organic polymer. The response can include a change in conductivity, resistance, impedance, capacitance, inductance, or optical properties of one or more of the sensors, or a combination thereof, upon exposure of the sensors to the chemical analyte. If the chemical analyte is smaller than the size of the chemical group, the response can be measured as a decrease in resistance or an increase in conductivity resulting from displacement of the chemical group by the chemical analyte. The nonconductive material can include a plurality of chemical groups coupled to the conductive material. The plurality of chemical groups can include a plurality of different chemical groups. The sensors can be exposed to the fluid containing the chemical analyte under conditions sufficient to cause the chemical analyte to displace a first portion of the plurality of chemical groups, such that the conductive material remains coupled to one or more remaining portions of the plurality of chemical groups. A second chemical analyte, which may be the same as or different from the first analyte, can be detected by exposing the sensors to a fluid containing the second chemical analyte under conditions sufficient to cause the second chemical analyte to displace one or more remaining portions of the plurality of chemical groups, and measuring a response based on the displacement of the one or more remaining portions of the plurality of chemical groups. The sensors can include a plurality of different sensors, and can take the form of a sensor array. The sensor array can include two or more sensors that include different conductive materials or chemical groups. The chemical analyte can be detected based on a different response measured for each of a plurality of the different sensors.

In general, in another aspect, the invention provides further sensors, sensor arrays and sensing methods for detecting a chemical analyte in a fluid. One or more sensors are provided, which include a plurality of conductive particles disposed in a nonconductive matrix. The conductive particles include a metallic core. The sensors are exposed to a fluid containing a chemical analyte under conditions sufficient to cause the chemical analyte to react with the metallic core to form a capped particle. A response is measured based on the reaction of the chemical analyte and the metallic core. The chemical analyte is detected based on the measured response.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
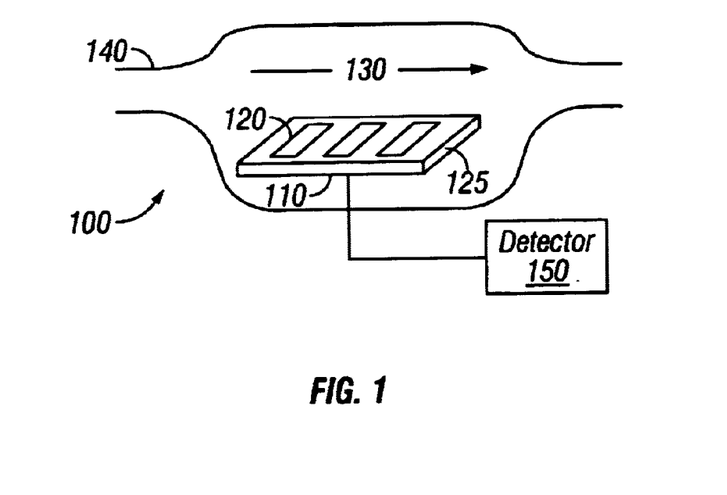
FIG. 1 is a schematic diagram of a sensor system for detecting an analyte in a fluid.

Referring to FIG. 1, one embodiment of a system 100 for detecting an analyte in a fluid includes a sensor array 110, including one or more sensors 120 arranged on a substrate 125 along a fluid channel 130. In some implementations, sensor array 110 may be configured to include one or more fluid channels in addition to fluid channel 130, which may include additional sensors arranged along the same or a different substrate. A fluid to be analyzed, which may be in gaseous or liquid form, is introduced to sensor array 110 through fluid inlet 140, for example from a fluid reservoir or the atmosphere. Response signals from the sensors 120 in sensor array 110 resulting from exposure of the fluid to the sensor array are received and processed in detector 150, which may include, for example, signal-processing electronics, a general- or special-purpose programmable digital computer system, or the like. The sensors 120 may include means of probing changes in the nanoparticle network, such as optical detectors, impedance detector, mass detectors, and the like.

Sensors 120 preferably include one or more chemiresistive sensors, each including at least first and second conductive leads electrically coupled to and separated by a chemically sensitive resistor. The leads may be any convenient conductive material, usually a metal, and may be interdigitated to manipulate the circuit resistance and maximize the signal to noise ratio.

The resistor element includes multiple alternating regions of conductive and nonconductive materials arranged transverse to the electrical path between the conductive leads. In a preferred embodiment, the conductive materials include a plurality of particles, such as a colloidal nanoparticle, and the nonconductive materials are arranged proximate to and at least partially surround the particles. As used herein the term "nanoparticle" refers to a conductive cluster, such as a metal cluster, having a diameter on the nanometer scale. Generally, the resistors are fabricated by blending, reacting, or otherwise combining a conductive material with a nonconductive material, such that the electrically conductive path between the leads coupled to the resistor is interrupted by gaps of non-conductive material. For example, in a colloid, suspension or dispersion of particulate conductive material in a matrix of nonconductive organic polymer material, the matrix regions separating the particles provide the gaps. The nonconductive gaps can range in path length from about 10 to 1,000 angstroms, usually on the order of 100 angstroms, providing individual resistance of about 10 to 1,000 mΩ, usually on the order of 100 mΩ, across each gap. The path length and resistance of a given gap is not constant, but rather is believed to change as the sensor interacts with an analyte, as will be described in more detail below.

In some embodiments, the nonconductive material is an insulator. Without being bound to any particular theory, it is believed that the electrical pathway that an electrical charge traverses between the two contacting electrodes traverses both the region of a conductor and the region of an insulator. In this embodiment, the conducting region can be anything that can carry electrons from atom to atom, including, but not limited to, a material, a particle, a metal, a polymer, a substrate, an ion, an alloy, an organic material, (e.g., carbon, graphite, etc.) an inorganic material, a biomaterial, a solid, a liquid, a gas or mixtures thereof. In some embodiments, metal particles are particularly preferred.

The nonconductive material can include anything that can impede electron flow from atom to atom, including, but not limited to, materials, such as organic, inorganic or biomaterials, polymers, plasticizers, fillers, ligands, solids, liquids, gases and mixtures thereof. In a preferred embodiment, the nonconductive material includes a chemical group coupled to the conductive material. The chemical group can be, for example, a ligand covalently coupled to a metal core (which can be said to be capped by the coupled ligands). Preferably, the chemical group is an organic ligand that is displaceable by an analyte—for example, an alkylamine that can be displaced by an alkane thiol using known place exchange chemistry. Optionally, sensors 120 can be formed from a matrix of organic polymers (which can include conducting, semiconducting, and/or insulating polymers) in which capped particles as described above are blended or embedded.

Organically capped metal nanoparticles include a small metal core (typically less than 10 nm in diameter) surrounded by a dense organic layer, which is coupled (e.g., through covalent bonds) to the metal surface. Capped nanoparticles incorporating a gold core are known, and are prepared through the sodium borohydride reduction of hydrogen tetrachloroaurate in the presence of a phase transfer reagent and a ligand precursor that will form the organic capping layer. Other metals have also been used, including platinum, silver, and palladium. In these applications, the most commonly used ligand precursor materials are straight alkyl chain thiols, as described, for example, in Brust et al., *J. Chem. Soc. Chem. Comm.* 1994, 801; other ligands, such as amines have also been used, as disclosed in Leff et al., *Langmuir* 1996, 12, 4723–4730. In a dry film of nanoparticles, the organic layer serves to separate the metal regions from each other. If the metallic regions of the particle come into contact with the metal regions of the neighboring nanoparticules, they irreversibly fuse together forming a continuous film. The organic layer surrounding the metal core must remain intact and well ordered to avoid this coalescence into bulk metal.

Figure 2:
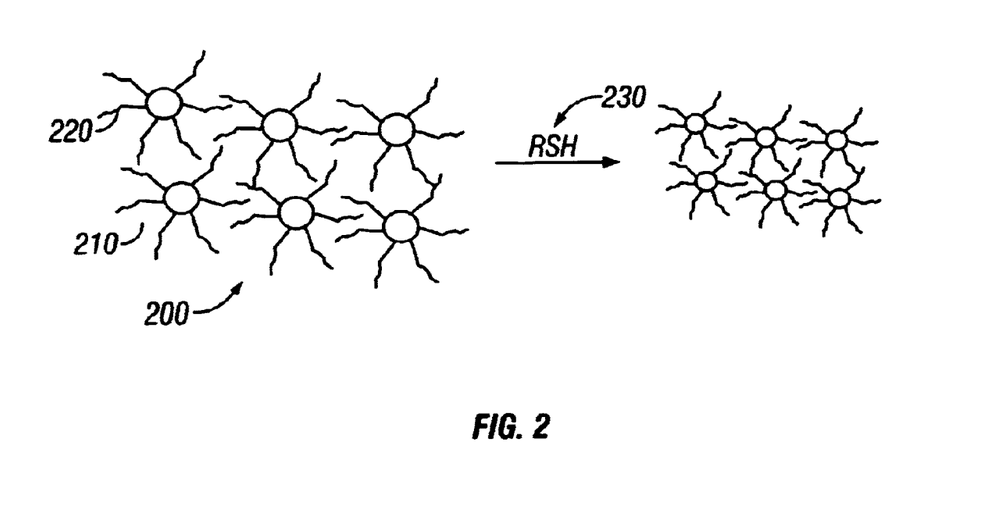
FIG. 2 is a schematic illustration of a place exchange reaction occurring upon exposure of a sensor film according to the present invention to a short-chain alkanethiol analyte in a fluid.

The sensitivity of capped nanoparticle films to the stability of their organic cap region, and the subsequent transition of isolated metal particles into a continuous metal film upon disruption of the cap region, also makes such films appropriate for use as a sensor mechanism, as illustrated in FIG. 2. Such materials are potentially useful as sensors because of the transition into metallic films upon exposure to vapors or liquids that induce a displacement and partial or complete loss of the organic region of the nanoparticule. Electrical properties (e.g., resistance, impedance, etc.) can be measured before, during, and after exposure to vapors, gases or liquids. Changes in these properties indicate the liquid or gas induced transition or partial transition of the nanoparticle film to a continuous or a semicontinuous metal film.

Prior to complete displacement of the capping region, a partial displacement can occur which permits the metal centers to move closer together without making contact. The organic cap region between adjacent particles has a large electrical resistance due to the tunneling of electrons though the organic layer. This resistance depends exponentially on the distance between adjacent particles; consequently, a slight decrease in the thickness of the organic layer, such as accompanies displacement of capping ligands 220 from metal particles 210 upon exposure of film 200 to thiol analyte 230, can translate into a large decrease in the bulk resistance of the film.

Thus, to provide for the detection of analytes, sensor array 110 includes one or more sensors 120 incorporating metal particles (also called "nanoparticles") that may be stabilized with one or more organic ligands. A variety of metals can be used to form conductive particles for use in sensors 120, including, for example, Au, Ag, Pt, Pd, Cu, Ni, W, Rh, Cr and alloys and mixtures thereof. For the detection of thiol-containing analytes, Au and Ag nanoparticles are particularly preferred. Without being bound to any particular theory, it is believed that exposure of a network of such metal nanoparticles, either alone or blended with organic polymers (either conducting, semiconducting, or insulating) to thiol-containing analytes results in the displacement of at least some of any species that are bonded to the nanoparticle along with the formation of thiolate bonds to the particles, thereby altering the conductive properties of the network. Measurement of the changes in these properties—for example, by measuring changes in conductivity, resistance, impedance, optical properties, or the like—thus provides a way to detect the presence of analytes that is specific to analytes capable of undergoing reactions with the nanoparticle's metal core. In some embodiments, these changes are not reversible, making the sensors appropriate for single-use analysis, but multiple responses may be possible for a given sensor.

Changes in conductivity of such capped particles blended with organic polymers (either conducting, semiconducting, or insulating), or of the capped particles by themselves, associated with the chemisorption of volatile sulfur vapors or other vapors that partially or fully displace the labile organic capping reagent can be used for obtaining enhanced sensitivity to selected analytes from such nanoparticle-based detectors. The presence of the vapor can also be detected optically or using other electrical methods such as impedance measurements.

Capped metal nanoparticles can be stabilized by a variety of ligands, including alkanethiols, alkylamines, phosphines, and dendrimers, as described, for example, in Templeton et al., *J. Am. Chem. Soc.* 1998, 120, 1906–1911; Lee et al., *Isr. J. Chem.* 1997, 37, 213–223; Hostetler et al., *Langmuir* 1998, 14, 17–30; Ingram et al., *J. Am. Chem. Soc.* 1997, 119, 9175–9178; Hostetler et al., *J. Am Chem. Soc.* 1996, 118, 4212–4213; Henglein, *J. Phys. Chem.* 1993, 97, 5457–5471; Zeiri, *J. Phys. Chem.* 1992, 96, 5908–5917; and Leff et al., *Langmuir* 1996, 12, 4723–4730, each of which is incorporated by reference herein. Such capped nanoparticles readily undergo place exchange reactions with stronger ligands, as described in Ingram et al., *J. Am. Chem. Soc.* 1997, 119, 9175–9178. Thus, exposure of nanoparticles capped with an insulating layer of organic ligands to analytes that can act as stronger ligands to the metal core will result in an exchange of the organic ligands that form the insulating layer with the more strongly bound analyte. In a preferred embodiment, where the organic layer is displaced by a thiol-containing analyte, a new insulating layer is formed comprising at least some thiolate ligands. Differences between the insulating properties of the new nanoparticle shell and the original nanoparticle shell can then be detected by measurement of changes in the conductivity, resistance, impedance, optical or other properties, as will be recognized by those skilled in the art.

In particular, such capped metal nanoparticle sensors can exploit the exponential distance dependence of conductivity on the core to core particle separation in composite films to detect the presence of volatile sulfur compounds. Without being bound to any particular theory, it is believed that long ligand shells are potent inhibitors of electrical conductivity. A decrease in the edge to edge distance between particles distance is expected to produce a large decrease in resistance. Thus, replacing long labile capping agents with smaller sulfur ligands derived from analyte-containing fluids is expected to produce a large signal with a magnitude inversely proportional to the size of the incoming molecule. In this type of signal transduction mode, the conductivity of the composite increases in response to the presence of compounds, such as thiols, that could displace the ligand groups on the surface of the metal particles in the composite films. Alternatively, long ligands can be used to increase the interparticle distance from particle networks that originally included short bound ligands or from naked nanoparticles without any chemically bonded shell species.

Examples of colloidal nanoparticles for use in accordance with the present invention are known, as described, for example, in the references cited above. The nonconductive region can optionally include one or more ligands that are attached to a central core making up the nanoparticle. These ligands, also referred to as caps, can be polyhomo or polyheterofunctionalized, thereby rendering them suitable for detecting a variety of chemical analytes. The nanoparticles, i.e., clusters, are stabilized by the attached ligands. As explained more fully below, by varying the concentration of the synthetic reagents, the particle size can be manipulated and controlled.

In certain embodiments, the sensors include nanoparticles comprising a central core conducting element and an insulating attached ligand optionally in a polymer matrix.

Metallic nanoparticles can be synthesized using a variety of methods. In a preferred method of synthesis, a modification of the protocol developed by Brust et al., *J. Chem. Soc., Chem. Commun.*, 1994, 801–802, which is incorporated by reference herein, can be used. Using alkanethiolate gold clusters as an illustrative example, and not in any way to be construed as limiting, the starting molar ratio of $HAuCl_4$ to alkanethiol is selected to construct particles of the desired diameter. The organic phase reduction of $HAuCl_4$ by an alkanethiol and sodium borohydride leads to stable, modestly polydisperse, alkanethiolate-protected gold clusters having a core dimension of about 1 nm to about 100 nm. Preferably, the nanoparticles range in size from about 1 nm to about 50 nm. More preferably, the nanoparticles range in size from about 5 nm to about 20 nm.

In this reaction, a molar ratio of $HAuCl_4$ to alkanethiol of greater than 1:1 leads to smaller particle sizes, whereas a molar ratio of $HAuCl_4$ to alkanethiol less than 1:1 yield clusters which are larger in size. Thus, by varying the ratio of $HAuCl_4$ to alkanethiol, it is possible to generate various sizes and dimensions of nanoparticles suitable for a variety of analytes. Although not intending to be bound by any particular theory, it is believed that during the chemical reaction, as neutral gold particles begin to nucleate and grow, the size of the central core is retarded by the ligand monolayer in a controlled fashion. Using this reaction, it is then possible to generate nanoparticles of exacting sizes and dimensions.

Ligands or caps of various chemical classes are suitable for use in the present invention. In one embodiment, the ligands are thiols or amines. More generally, ligands can include, but are not limited to, thiols, amines and other species that form displaceable chemical bonds to the particles in the network, having alkyl chain lengths of about $C_1$–$C_{30}$. In a preferred embodiment, the chain lengths of the capping species are between about $C_3$ to about $C_{12}$. In this embodiment, it is noted that the conductivity of the material decreases as alkane length increases.

Capping species suitable for use can also be polyhomofunctionalized or polyheterofunctionalized (such as, at the $\Omega$-position, or last position of the chain). As used herein, the term "polyhomofunctionalized" means that the same chemical moiety has been used to modify the ligand at various positions within the ligand. Chemical moieties suitable for functional modification include, but are not limited to, bromo, chloro, iodo, fluoro, amino, hydroxyl, thio, phosphino, alkylthio, cyano, nitro, amido, carboxyl, aryl, heterocyclyl, ferrocenyl or heteroaryl. The ligands can be attached to the central core by various methods including, but not limited to, covalent attachment, and electrostatic attachment. As used herein, the term "polyheterofunctionalized" means that different chemical moieties or functional groups are used to modify the ligands at various positions.

It is possible to synthesize polyheterofunctionalized clusters via place exchange reactions, as described in Ingram et al., *J. Am. Chem. Soc.*, 1997, 119, 9175–9178. This reaction can be a simultaneous exchange of a mixture of capping agents onto the nanoparticle, or alternatively, a stepwise progressive exchange of different capping agents, isolating the nanoparticle product after each step. The place exchange reaction replaces an existing capping species, preferably an amine or alkanethiol, with a capping species comprising a functional group.

Suitable capping ligands include, but are not limited to, straight chain or branched alkyl amines or alkyl thiols, which may optionally include one or more of the following: alkynes; alkenes; branched alkanes; branched alkenes; branched alkynes; amines; halides; aromatics; alcohols; ethers; aldehydes; ketones; acids; ethers; aldehydes; ketones; acids; esters; nitriles; amides; thiols; carboxylates; nucleic acids; sulfonic acids; sulfonyl chlorides; thioketals; and peptides. Other suitable capping ligands can include, for example, phosphines, such as trioctylphosphines or tributylphosphines, carboxylates, thiolates, nitrites, sulfonates, and surfactants. Those skilled in the art will recognize that the choice of a particular metal and/or ligand will depend on the particular application, such as the nature of the particular analyte being investigated or the environment in which the analyte is to be detected.

For thiol-sensing embodiments, the preferred capping ligands are amines, which form capped metal nanoparticles that are inherently less stable than the analogous thiolate-capped particles that result from place exchange with thiol-containing analytes. As analyte molecules (which may be small thiols, such as hydrogen sulfide or methanethiol, but which may also include larger thiol-containing species) diffuse into the cap layer and reach the interface of the cap layer and the metal, they displace some or all of the larger weakly bound alkyl amines that form the cap region. This results in either of, or both of the above processes and the associated resistance change which is easily recorded.

The rate and/or extent of the place exchange reaction between the analyte and capping ligands, and the resulting sensor response to particular thiol-containing analytes, can be influenced by a variety of factors, including, for example, the chemical identity and structure of the metal core and capping ligands, and the properties of the bonds between the core and ligand cap. Accordingly, those skilled in the art will recognize that sensor response and stability can be tuned for particular analytes by selecting among different metals for the nanoparticle core—for example, using platinum, silver or palladium instead of gold. Similarly, the strength of the bond between the capping ligands and the metal core can be adjusted by changing the nature of the precursor molecule which becomes the cap region of the nanoparticule. Ligands containing longer chains may be more crystalline and hydrophobic, and may therefore hinder large or polar analytes from enacting the transition. Ligands that contain shorter chains, units of unsaturation, or branches can disrupt the cap region, making it easier for analyte molecules to diffuse through to the core. Ligands having plasticizer-like characteristics can likewise change the properties of the capping layer, and therefore the rate at which different analytes move through the capping layer. Temperature and pressure may also influence the process.

In certain embodiments, the core, such as a metal core, acts as a scaffolding, which can support more complex organic ligands. These scaffolding can be used as a solid support for combinatorial synthesis. In this embodiment, various functional groups can be attached to the core to achieve structural diversity. Optionally, the combinatorial synthesis can be performed using a robotic armature system. In general, these systems include automated workstations like the automated apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual operations performed by a synthetic chemist. The nature and implementation of modifications to these methods (if any) so that they can operate will be apparent to persons skilled in the relevant art.

It is possible that steric crowding can accompany the introduction of numerous functional groups onto the surface of the nanoparticle core that is occupied by the ligand, such as athiolate or amine ligand. The number of ligands and the amount of functionalization is directly proportional to the size of the central core. In practice, electrical conductivity becomes more difficult to measure when the ratio of metal to ligand decreases. Conversely, as the ratio of metal to ligand increases, the core can become too big to allow the ligands to solubilize the particle. Thus, those of skill in the art will select suitable ratios of core size to ligand amount for particular uses.

In certain other embodiments, sensors are prepared as composites of "naked" nanoparticles and an insulating material is added. As used herein, the term "naked nanoparticles" means that the core has no covalently attached ligands or caps. A wide variety of insulating materials can be used in this embodiment. Preferred insulating materials are organic polymers. Suitable organic polymers include, but are not limited to, polycaprolactone, polystyrene, and poly(methyl methacrylate). Varying the insulating material types, concentration, size, etc., provides the diversity necessary for an array of sensors. In one embodiment, the metal to insulating polymer ratio is about 50% to about 90% (wt/wt). Preferably, the metal to insulating polymer ratio is about 85% to about 90% (wt/wt).

Sensors can also be prepared using the nanoparticle and a capping species as the sole insulating matrix. In this embodiment, varying the ligand, ligand size and functionalization can provide sensor diversity. Sensor films can be cast on interdigitated electrode substrates. Sensors that are comprised either of naked nanoparticles or nanoparticles having ligands show a change in electrical resistance upon exposure to chemical vapors. Moreover, it has been shown that as the length of the ligand chain increases, the conductivity of the resistors decreases.

Nanoparticles, such as alkylthiol-capped gold colloids, are soluble or dispersible in a wide range of organic solvents having a large spectrum of polarity. This diverse solubility permits a good selection of co-soluble insulating materials. Alternative capping agents, such as those described above, can extend the use to virtually any solvent. Simultaneous variation of ligand and insulating material, such as organic polymers, can provide great diversity in multidimensional sensor arrays.

Without intending to be bound by any particular theory, it is believed that the chemical analyte diffuses into and is dispersed within the nanoparticle ligands or insulating material that make up the nonconductive regions. The ligands or other nonconductive material in the nonconductive regions may be displaced by the analyte through a place exchange reaction as discussed above, resulting in changes in the sensor's electrical properties. The dynamic aggregate resistance provided by the gaps in a given resistor is a linear or non-linear function of the reaction between the the analyte and the nanoparticle regions. In some embodiments, the conductive material may also contribute to the dynamic aggregate resistance as a linear or nonlinear function of analyte permeation (e.g., when the conductive material is a conductive organic polymer, such as polypyrrole). These property changes which are then detected include, but are not limited to, resistance, capacitance, conductivity, magnetism, optical changes and impedance.

Optionally, sensors 120 can also include one or more sensors of any of a variety of other known types, including, for example, surface acoustic wave sensors, quartz crystal resonators, metal oxide sensors, dye-coated fiber optic sensors, dye-impregnated bead arrays, micromachined cantilever arrays, vapochromic metalloporphyrins, composites having regions of conducting material and regions of insulating organic material, composites having regions of conducting material and regions of conducting or semiconducting organic material, chemically-sensitive resistor or capacitor films, metal-oxide-semiconductor field effect transistors, bulk organic conducting polymeric sensors, and other known sensor types. Techniques for constructing arrays of such sensors are known, as disclosed in Harsanyi, *Polymer Films in Sensor Applications* (Technomic Publishing Co., Basel, Switzerland, 1995), and U.S. Pat. No. 6,017,440, 6,013,229 and 5,911,872 and co-pending U.S. patent application Ser. No. 09/409,644, filed Oct. 1, 1999, which are incorporated by reference herein. Techniques for fabricating particular sensor types are disclosed in Ballantine, et al., *Anal. Chem.* 1986, 58, 3058; Grate, et al., *Sens. Actuators B* 1991, 3, 85; Grate, et al., *Anal. Chem.* 1993, 65, 1868; Nakamoto, et al., *Sens. Actuators B* 1993, 10, 85 (surface acoustic wave (SAW) devices), Gardner, et al., *Sens. Actuators B* 1991, 4, 117; Gardner, et al., *Sens. Actuators B* 1992, 6, 71; Corcoran, et al., *Sens. Actuators B* 1993, 15, 32 (tin oxide sensors), Shurmer, et al., *Sens. Actuators B* 1991, 4, 29; Pearce, et al., *Analyst* 1993, 118, 371 (conducting organic polymers), Freund, et al., *Proc. Natl. Acad. Sci.* 1995, 92, 2652 (materials having regions of conductors and regions of insulating organic material), White, et al., *Anal. Chem.* 1996, 68, 2191 (dye-impregnated polymer films on fiber optic sensors), Butler, et al., *Electrochem. Soc.* 1990, 137, 1325; Hughes, et al., *Biochem. and Biotechnol.* 1993, 41, 77 (polymer-coated micromirrors), Slater, et al., *Analyst* 1994, 119, 191; Slater, et al., *Analyst* 1991, 116, 1125 (quartz crystal microbalances (QCMs)), Keyvani, et al., *Sens. Actuators B* 1991, 5, 199 (electrochemical gas sensors), Zubkans, et al., *Thin Solid Films 1995, 268, 140* (chemically sensitive field-effect transistors) and Lonergan, et al., *Chem. Mater.* 1996, 8, 2298 carbon black-polymer composite chemiresistors ). Additional sensor array fabrication techniques are disclosed in Albert, et al., *Chem. Rev.* 2000, 100, 2595–2626 and the references cited therein. In other embodiments, these foregoing sensor types comprise nanoparticles of the present invention.

The chemiresistors of the present invention can be fabricated by many techniques including, but not limited to, solution casting, suspension casting and mechanical mixing. In general, solution casting routes are advantageous because they provide homogeneous structures and are easy to process. With solution casting routes, resistor elements can be easily fabricated by spin, spray or dip coating. Since all elements of the resistor must be soluble, however, solution casting routes are somewhat limited in their applicability. Suspension casting still provides the possibility of spin, spray or dip coating, but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting and non-conducting media or their reaction precursors are soluble in a common solvent, the chemiresistors can be fabricated by solution casting.

In suspension casting, one or more of the components of the resistor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the assembly of particles and capping species and any insulator is dissolved in an appropriate solvent (such as THF, acetonitrile, water, etc.). The resulting mixture is used to dip coat substrates.

Mechanical mixing is suitable for the conductive/non-conductive combinations. In this technique, the materials are physically mixed in a ball-mill or other mixing device. For instance, carbon black/non-conductive polymer composites are readily made by ball-milling. When the non-conductive polymer and/or capping reagent can be melted or significantly softened without decomposition, mechanical mixing at elevated temperatures can improve the mixing process. Alternatively, composite fabrication can sometimes be improved by several sequential heat and mix steps.

For the nanoparticles with and without ligands, spray deposition can be used. In this method, the temperature can be elevated to promote a uniform film formation. The stable dispersions and homogenous films of these nanoparticles can also facilitate reproducible fabrication of the vapor sensors.

Once fabricated, the individual elements can be optimized for a particular application by varying their chemical make up and morphologies. The chemical nature of the resistors determines to which analytes they will respond and their ability to distinguish different analytes. The relative ratio of conductive to insulating components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalogue of information on chemically diverse sensors made with varying ratios of insulating to conducting components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The sensor may itself form a substrate for attaching the lead or the sensor. For example, the structural rigidity of the resistors may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high transition metal (Tm) polymers), the incorporation of the resistor elements into supporting matrices, such as clays or polymer networks (forming the resistor blends within poly(methylmethacrylate) networks or within the lamellae of montmorillonite, for instance), etc. In another embodiment, the sensor is deposited as a surface layer on a solid matrix that provides means for supporting the leads. Typically, the solid matrix is a chemically inert, non-conductive substrate, such as a glass or ceramic.

Sensor arrays particularly well-suited to scaled up production are fabricated using integrated circuit (IC) design technologies. For example, chemiresistors can easily be integrated onto the front end of a simple amplifier interfaced to an A/D converter to efficiently feed the data stream directly into a neural network software or hardware analysis section. Micro-fabrication techniques can integrate chemiresistors directly onto a micro-chip which contains the circuitry for analogue signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different capping agents and/or insulators in solution which can be deposited are used. A sensor array of a million distinct elements only requires a 1 cm×1 cm sized chip employing lithography at the 10 $\mu$m feature level, which is within the capacity of conventional commercial processing and deposition methods. This technology permits the production of sensitive, small-sized, stand-alone chemical sensors.

Preferred sensor arrays have a predetermined inter-sensor variation in the structure or composition of the nonconductive organic polymer regions. The variation may be quantitative and/or qualitative. For example, the concentration of a nonconductive organic polymer or of a capping species can can be varied across sensors. Alternatively, a variety of different insulating or conducting species can be used in different sensors.

In certain embodiments, a variety of capped colloids can be used as different sensors. Optionally, a capped colloid system can be used in conjunction with a variety of polymer matrices as different sensors. An sensor array for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically, such an array comprises at least ten, often at least 100, and sometimes at least 1000 different sensors, though with mass deposition fabrication techniques described herein or otherwise known in the art, arrays of on the order of at least $10^6$ sensors are readily produced.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising a different chemical analyte or the same chemical analyte at a second different concentration. The fluids may be liquid or gaseous in nature.

The first and second fluids may reflect samples from two different environments, a change in the concentration of an analyte in a fluid sampled at two time points, a sample and a negative control, etc. Single sensors of the type disclosed herein can be used to determine the presence of a particular analyte of interest to which the sensor responds. Use of a sensor array necessarily comprises use of sensors which respond differently to a change in an analyte concentration, i.e., the difference between the first and second electrical resistance of one sensor is different from the difference between the first and second electrical resistance of another sensor.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

A wide variety of analytes and fluids may be analyzed by the disclosed sensors and sensor arrays so long as the subject analyte is capable of generating a differential response across a plurality of sensors of the array. Analyte applications include broad ranges of chemical classes including, but not limited to organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc., biomolecules such as sugars, isoprenes and isoprenoids, fatty acids and derivatives, etc. Accordingly, commercial applications of the sensors and sensor arrays include environmental toxicology and remediation, biomedicine, materials quality control, food and agricultural products monitoring, and the like.

A preferred method for using the disclosed sensors and sensor arrays for detecting the presence of an analyte in a fluid involves sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

The following examples are offered by way of illustration and not by way of limitation.

EXAMPLES

Sensor arrays for detecting thiol-containing ligands were prepared by depositing films of amine-capped gold nanoparticles onto insulating glass substrates between conductive contact lines coupled to a detector for measuring changes in electrical resistance. The sensor films were exposed to flowing streams of dilute vapors of methane thiol, hydrogen sulfide, and longer alkyl thiols. The resposes were taken as the slope of a line fit to the natural log of the resistance in a period shortly after initiating the exposure to the vapors.

The line was fit over the data points in the region in which the sensor resistance fell from 95% to 85% of the average preexposure value. The chosen analytes were delivered at a constant total flow rate over the sensors, but at different concentrations. The sensor descriptor was linear vs. concentration for methane thiol over a range of concentrations using several detectors.

Amine capped gold nanoparticles were prepared without a phase transfer reagent according to the procedure of Leff et al., *Langmuir* 1996, 12, 4723–4730, using decylamine or dodecylamine (Aldrich), a gold salt (hydrogen tetrachloroaurate) (Johnson-Mathey), and sodium borohydride (Aldrich). Films were prepared by placing drops of a toluene or hexane solution on an interdigitated electrode (formed from 20 thin gold lines each separated by 10 microns on a glass substrate). These sensors were placed in a row in a small linear chamber. The resistance was measured with a HP 34970a multiplexing digital multimeter (Hewlet Packard). Gases such as hydrogen sulfide and methyl mercaptan were purchased from Matheson in nitrogen at these concentrations: (methanethiol 958.4 ppm) (methanethiol 10.5 ppm)($H_2S$ 1080 ppm). These gases were further diluted with lab air using mass flow controllers (Unit). 28 SLM (standard liter per minute), 626 scam (standard cubic centemeter per minute), 60 sccm, and 8 sccm mass flow controllers were used to achieve the appropriate dilution. Thiol vapors from liquids such as propane thiol (Aldrich) were generated by bubbling air through a column of the liquid. Saturation of this bubbler output was confirmed with a flame ionization detector (California Analytical), and this output was diluted by mixing with air from a second mass flow controller (Unit). The total flow rate into the chamber and over the sensors was held constant at 4 SLM before during and after exposure. Typical exposures were 30s, 60s, or 300s, in duration. Each sensor was exposed only once, then discarded.

In one experiment, a 500 ml round bottomed flask was charged with hydrogen tetrachloroaurate (0.4234 g) in 100 ml deionized water. Dodecylamine (2.1884 g) was added in 100 ml toluene. Sodium borohydride (0.6241 g) was added in an additional 100 ml of DI water over a period of about 90 seconds. Foaming was observed, and the reaction mixture was transferred to a 2000 ml round bottomed flask 100 ml of toluene was then added to the mixture. The reaction mixture became blackish purple after about 5 minutes. After 14 hours, the organic phase was separated and concentrated to about 3–5 ml. The product was precipitated in 800 ml of 95% ethanol in the freezer. The precipitated product was collected on nylon filter paper (0.45 pm) and redissolved in hexane. The resulting suspension was dried by rotary evaporation. Yield was 0.0472 g. Sensors prepared by depositing the product on interdigitated electrodes prepared by grounding the tops off of capacitors showed a baseline resistance of greater than 100 MΩ. Upon exposure to gas phase streams of thiols, these sensors showed dramatic decreases in resistance as described below.

Figure 3:
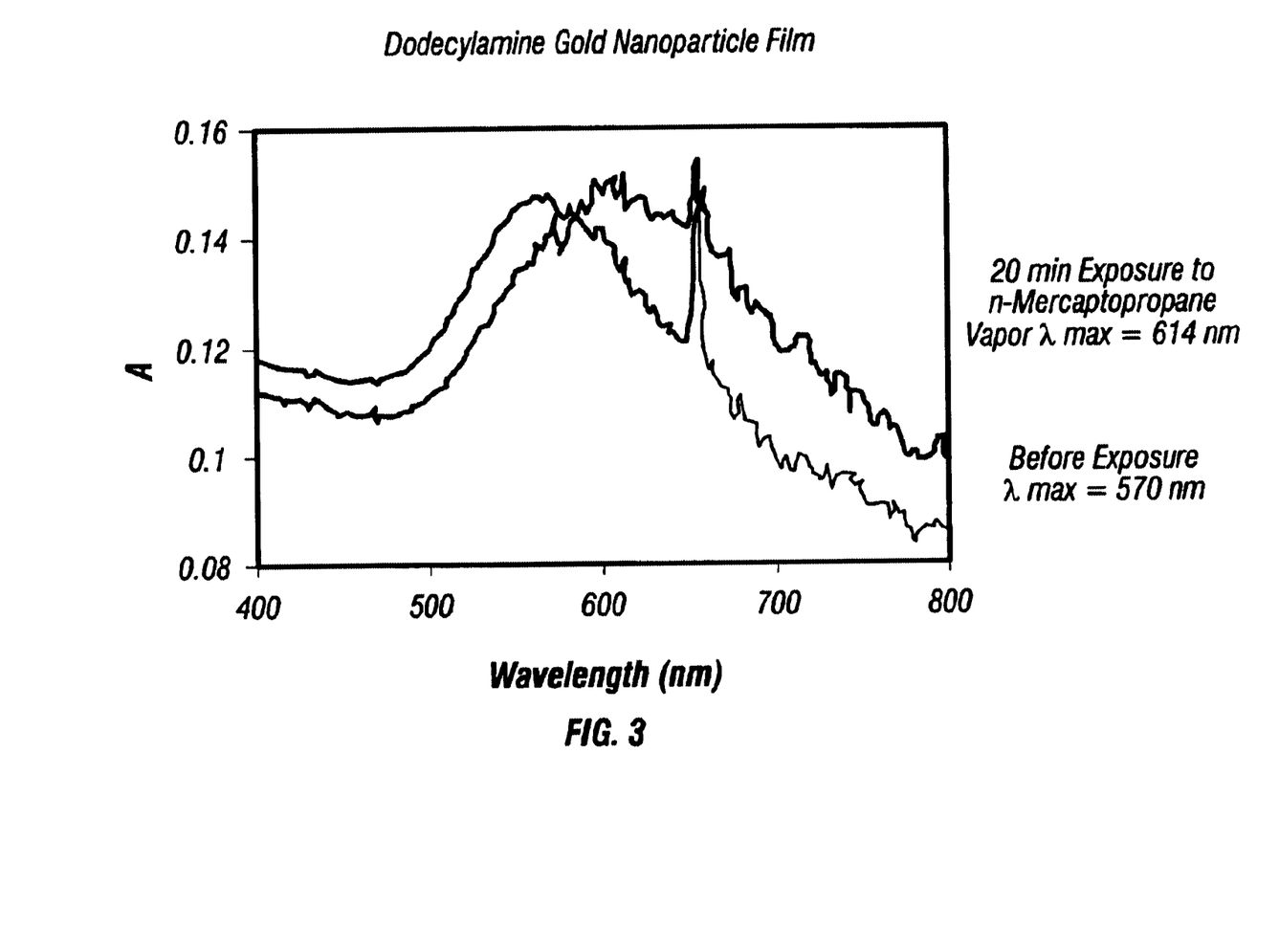
FIG. 3 illustrates a shift in the UV-Visible spectrum observed for a thin film of dodecylamine capped gold particles upon exposure to a vapor of propanethiol, showing a shift in color from red to blue.

Exposure of thin films consisting of dodecylamine capped Au nanoparticles produced as described above to a stream of propanethiol (n-mercaptopropane) vapor resulted in a change in the observed UV-Visible spectrum as illustrated in FIG. 3, reflecting a change in color of the exposed area from red to blue. This is believed to be associated with the displacement of some or all of the weakly-bound dodecylamine ligands in the capping shell by smaller propanethiolate ligands derived from the vapor.

Figure 4A:
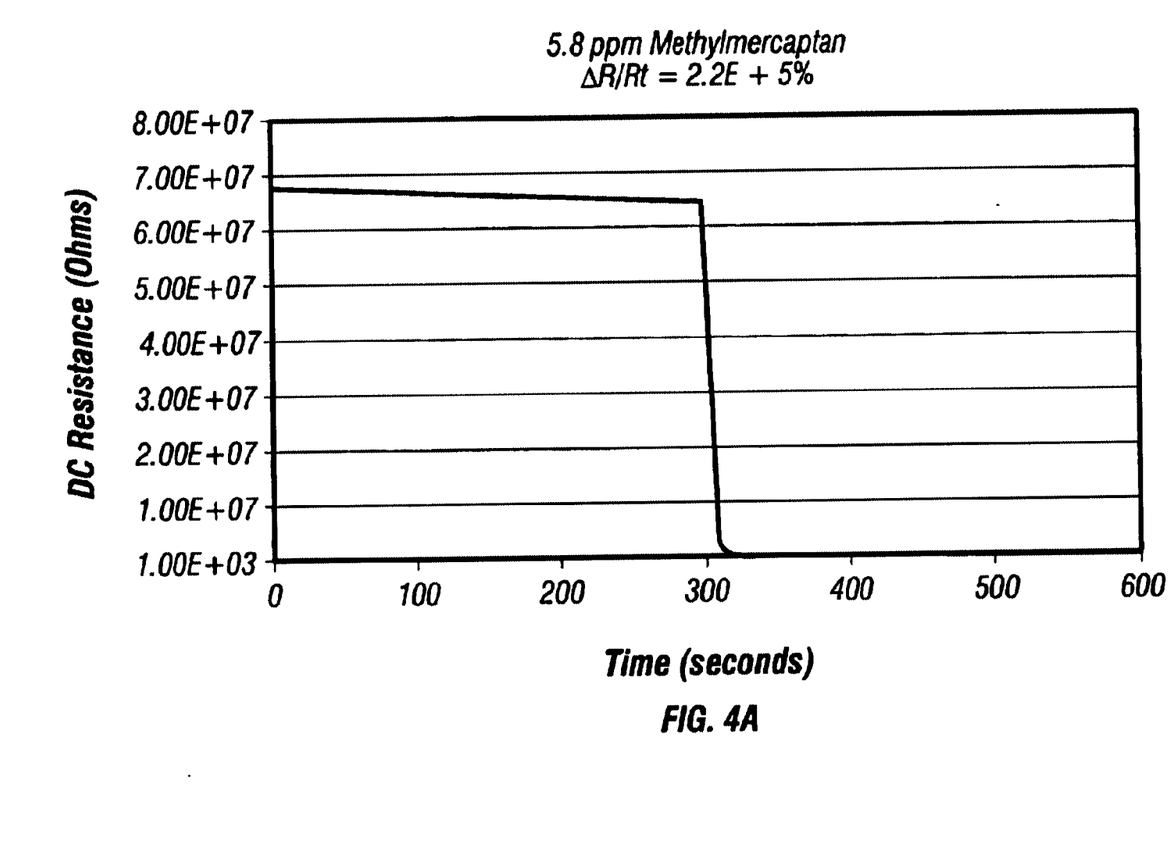
FIGS. 4A and 4B are plots of resistance response for a 300 second exposure of a dodecylamine capped nanoparticle sensor film to a stream of air containing 5.8 ppm methanethiol.
Figure 4B:
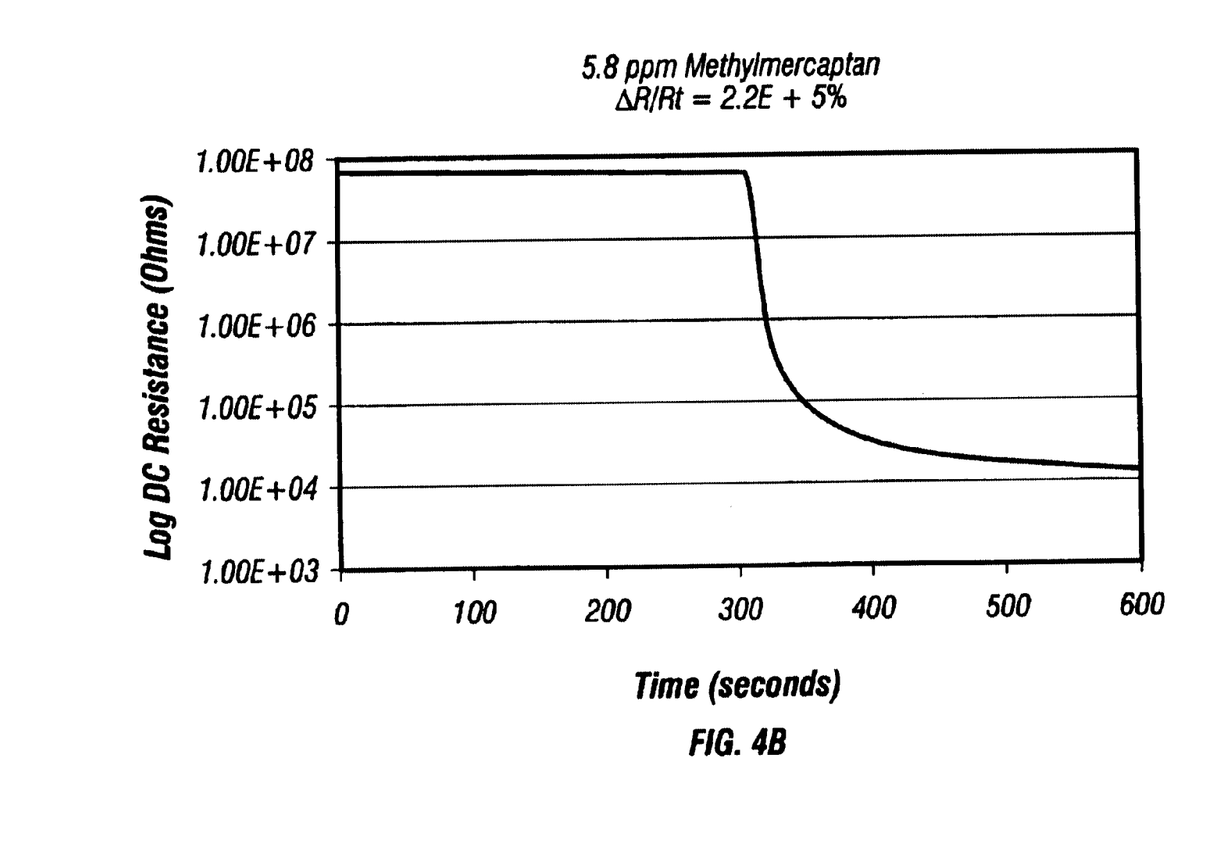

FIG. 4A illustrates resistance measurements for a typical experiment, in which a thin film of dodecylamine capped Au nanoparticles prepared as described above was exposed to a stream of air containing 5.8 ppm of methanethiol (methylmercaptan) for an exposure time of 300s. FIG. 4B is a logarithmic plot showing the same data.

Figure 5:
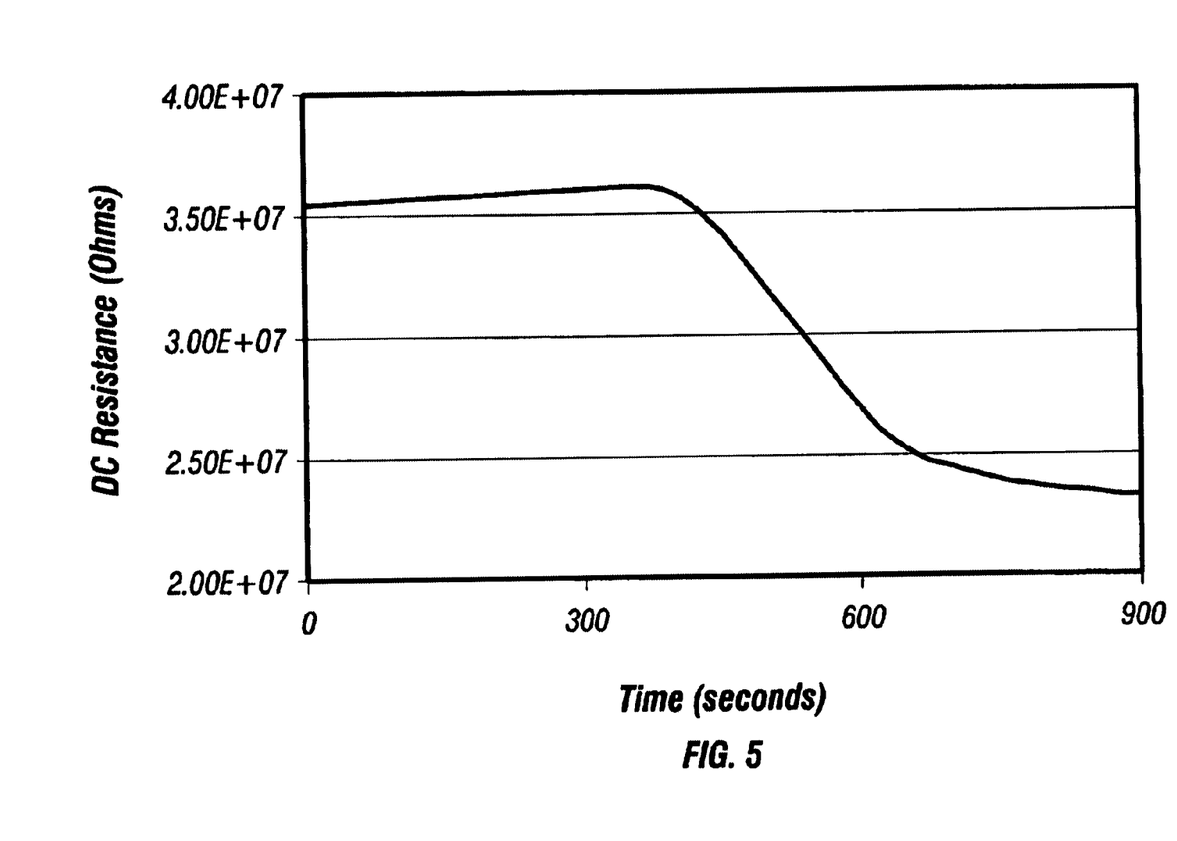
FIG. 5 is a plot of resistance response for a dodecylamine capped nanoparticle sensor film exposed to a stream of air containing 48 ppb methanethiol.
Figure 6:
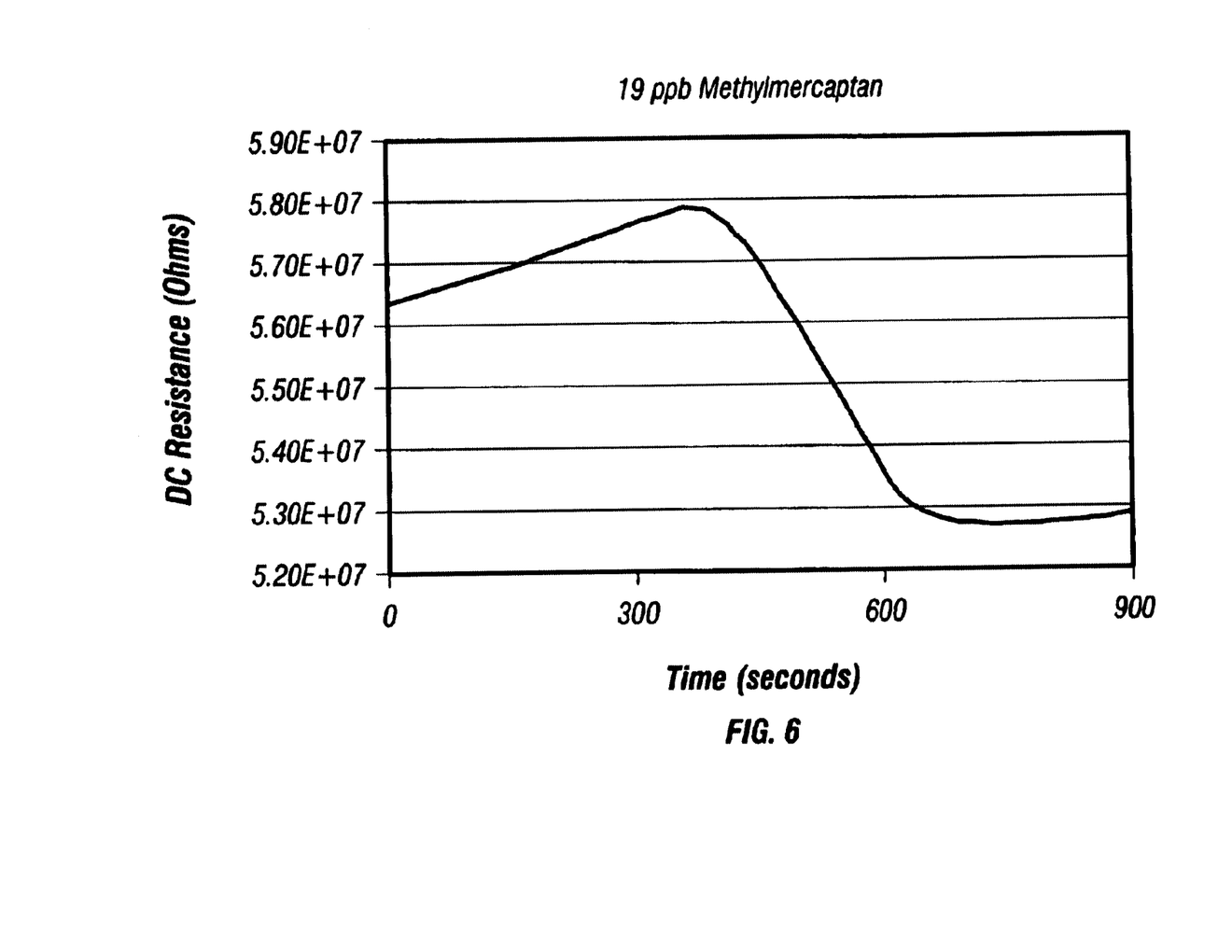
FIG. 6 is a plot of resistance response for a dodecylamine capped nanoparticle sensor film exposed to a stream of air containing 19 ppb methanethiol.

FIG. 5 illustrates resistance measurements for the exposure of a thin film of dodecylamine capped Au nanoparticles prepared as described above to a stream of air containing 48 ppb methanethiol. FIG. 6 illustrates the exposure of a similar film to a stream of air in which methanethiol was present at a concentration of 19 ppb.

Figure 7A:
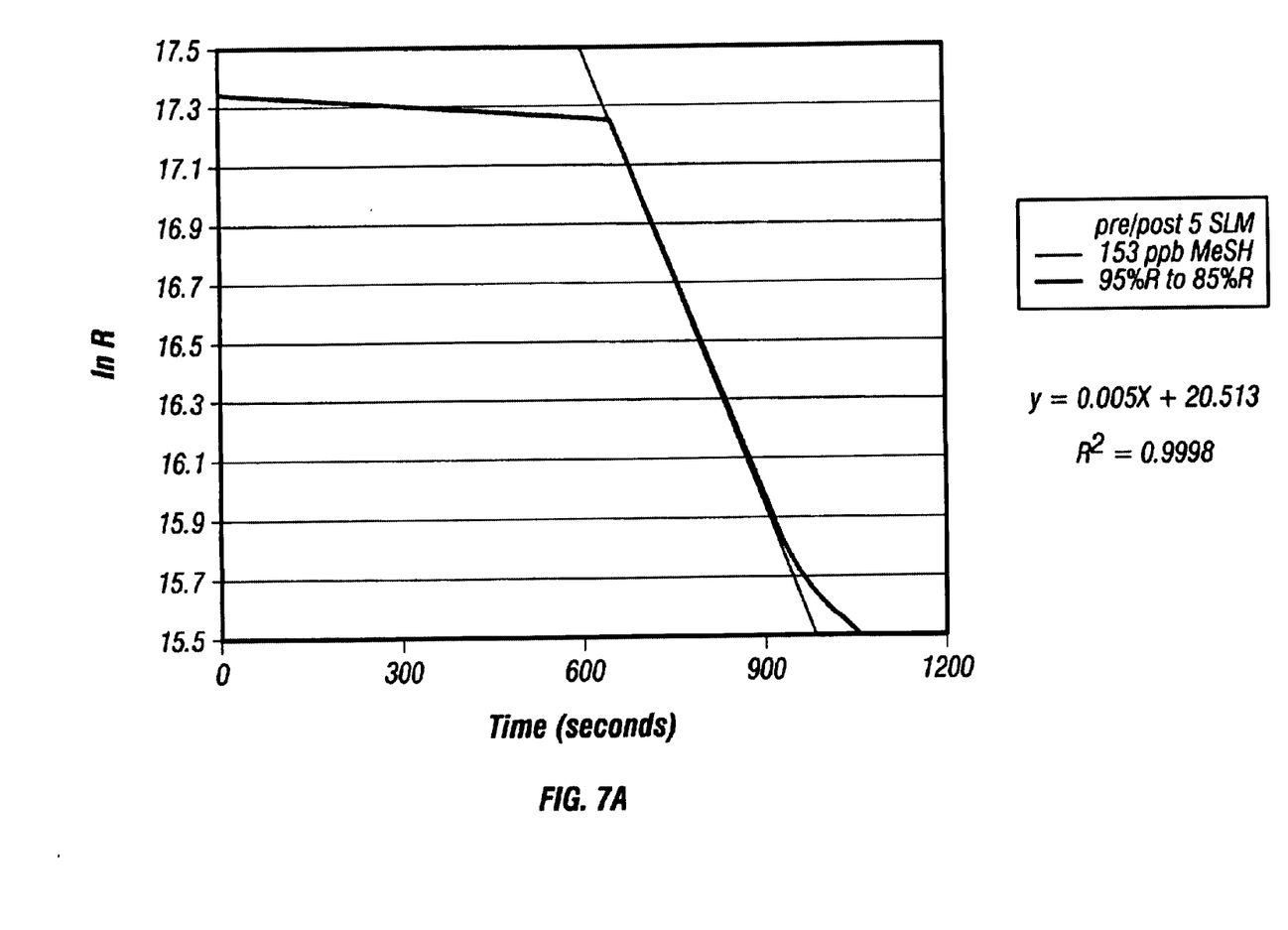
FIG. 7A is a plot of resistance response for a dodecylamine capped nanoparticle sensor film exposed to a stream of air containing 153 ppb methanethiol.
Figure 7B:
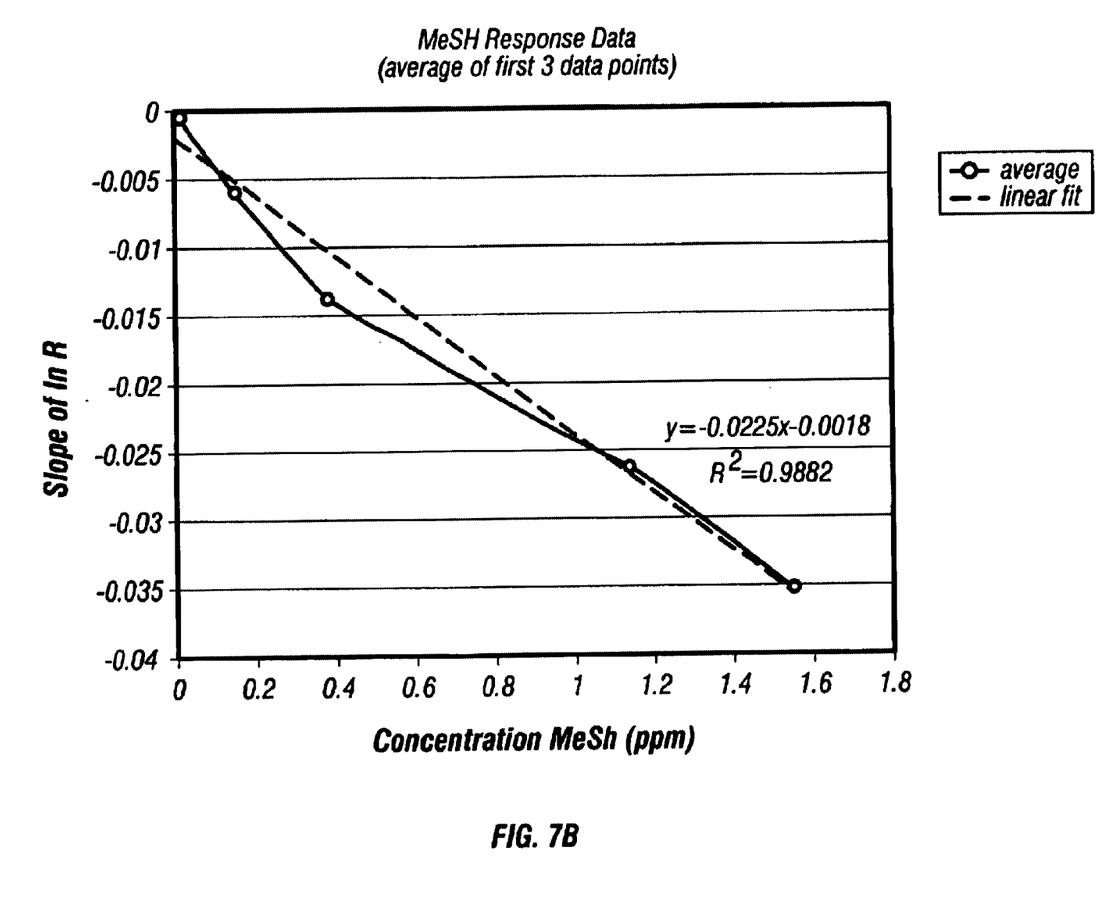
FIG. 7B is a plot of the slope of lnR vs concentration of methanethiol for the experiment of FIG. 7A.

FIG. 7A illustrates resistance measurements for the exposure of a dodecylamine capped Au nanoparticle thin film to a stream of air containing 153 ppb methanethiol as described above. The slope of lnR vs concentration of methanethiol is plotted in FIG. 7B, demonstrating a logarithmic relationship between resistance and analyte concentration.

Figure 8:
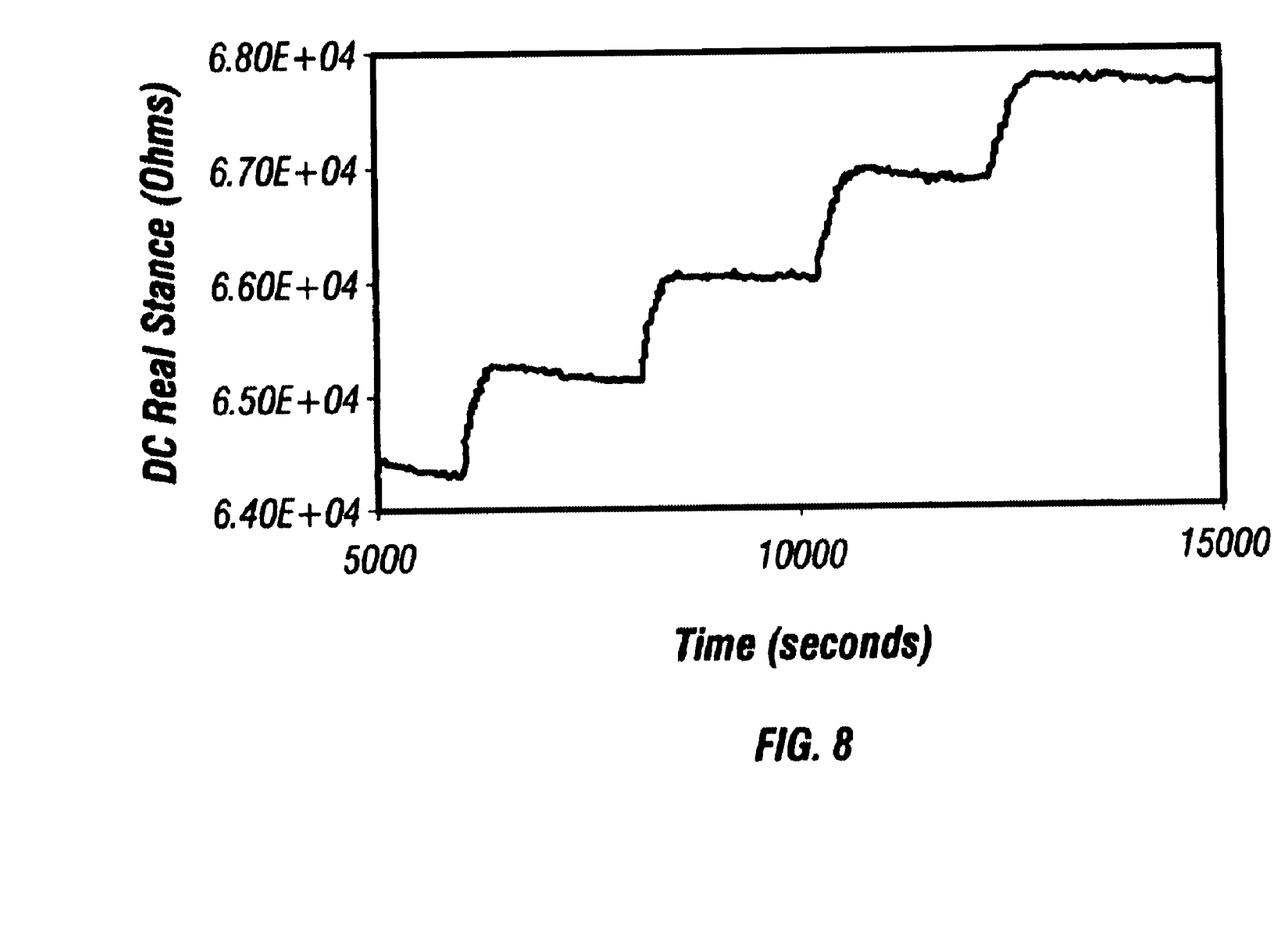
FIG. 8 is a plot of resistance response for an amine capped nanoparticle sensor film (after baking for 5 to 20 seconds) exposed to multiple presentations of a stream of air containing 1.9 ppm of methanethiol.

FIG. 8 is a plot of resistance measured for repeated exposures of capped gold nanoparticle sensors to methanethiol at a concentration of 1.9 ppm in air. Sensors were prepared as decyl or dodecyl amine capped nanoparticles films (prepared as described above) on gold glass substrates. The initial resistance was greater than 100 MΩ. Because this exceeded the measurement threshhold, the sensors were heated on a hot plate at approximately 120° C. for 5 to 20 seconds until they produced a suitable measured resistance (typically less than 1 MΩ).

Subsequent exposure to thiols such as methanethiol and propanethiol resulted in increases in resistance, as shown in FIG. 8 for methanethiol.

Without intending to be bound by theory, it is believed that the decrease in resistance upon heating is due, at least in part, to the loss of a portion of the capping layer, which allowed some of the particles to come together. The subsequent increase in resistance upon exposure to thiol vapors results from reaction of the thiol with the metal core, through one or more (or a combination of) possible mechanisms. in one possible mechanism, the addition of methanethiolate ligands to the metal surface increases the inter-core distance, thereby increasing resistance; alternatively, it is possible that the resistance changes result from chemisorbtion of thiols onto the surface of a very metallic thin film produced by baking off the amine capping ligands. In such films (e.g., on the order of the mean free path of an electron), conductivity is known to be very sensitive to surface properties.

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting a chemical analyte in a fluid, comprising:

providing one or more sensors comprising regions of conductive metal material and regions-of nonconductive material proximate to the conductive metal material, the nonconductive material including one or more chemical groups comprising one or more ligans coupled to the conductive metal material, the chemical groups being displaceable by a chemical analyte;

exposing the sensors to a fluid containing the chemical analyte under conditions sufficient to cause the chemical analyte to displace one or more of the chemical groups;

measuring a response based on the displacement of the chemical groups; and detecting the chemical analyte based on the measured response.

2. The method of claim 1, wherein:

the conductive metal material includes a plurality of particles comprising one more metals.

3. The method of claim 2, wherein:

the particles include a metal core; and the ligands are covalently coupled to the metal core.

4. The method of claim 3, wherein:

the chemical analyte is a thiol;

the metal core includes gold or silver; and the chemical groups include an alkylamine.

5. The method of claim 3, wherein:

the particles are disposed in a polymer matrix.

6. The method of claim 5, wherein:

the polymer matrix includes a conducting, semiconducting, or insulating organic polymer.

7. The method of claim 3, wherein:

the chemical analyte has a size that is smaller than a size of one or more of the chemical groups; and measuring the response includes measuring a decrease in resistance or an increase in conductivity resulting from displacement of the chemical groups by the chemical analyte.

8. The method of claimed 3, wherein:

the metals include one or more of Ag, Au, Cu, Pt, Pd, Ni, W, Rh, Cr and alloys and mixtures thereof.

9. The method of claim 3, wherein:

the ligands include one or more members selected from the group consisting of alkylamines, alkanethiols, phosphines, carboxylates, thiolates, nitrites, sulfonates and surfactants.

10. The method of claim 1, wherein:

measuring the response includes measuring a change in conductivity, resistance, impedance, capacitance, inductance, or optical properties of one or more of the sensors, or a combination thereof, upon exposure of the sensors to the chemical analyte.

11. The method of claim 1, wherein:

the nonconductive material includes a plurality of chemical groups coupled to the conductive metal material.

12. The method of claim 11, wherein:

the plurality of chemical groups includes a plurality of different chemical groups.

13. The method of claim 11, wherein:

the sensors are exposed to the fluid containing the chemical analyte under conditions sufficient to cause the chemical analyte to displace a first portion of the plurality of chemical groups, such that the conductive metal material remains coupled to one or more remaining portions of the plurality of chemical groups;

the method further comprising detecting a second chemical analyte by exposing the sensors to a fluid containing the second chemical analyte under conditions sufficient to cause the second chemical analyte to displace one or more remaining portions of the plurality of chemical groups, measuring a response based on the displacement of the one or more remaining portions of the plurality of chemical groups, and detecting the second chemical analyte based on the measured response.

14. The method of claim 13, wherein:

the second chemical analyte is the same as the chemical analyte.

15. The method of claim 13, wherein:

the second chemical analyte is different from the chemical analyte.

16. The method of claim 1, wherein:

the sensors include a plurality of different sensors.

17. The method of claim 16, wherein:

the plurality of different sensors form a sensor array.

18. The method of claim 17, wherein:

the sensor array includes two or more sensors each including a different conductive metal material.

19. The method of claim 17, wherein:

the sensor array includes two or more sensors each including a different chemical group.

20. The method of claim 17, wherein:

detecting the chemical analyte based on the measured response includes identifying the chemical analyte based on a different response measured for each of a plurality of the different sensors.

21. A method for detecting a chemical analyte in a fluid, comprising:

providing one or more sensors comprising a plurality of conductive metal particles disposed in a nonconductive matrix, the conductive metal particles comprising a metal core bounded to a chemical group;

exposing the sensors to a fluid-containing the chemical analyte under conditions sufficient to cause the chemical analyte to react with the metal particle 5 to form a capped particle metal cores by displacing the chemical groups with the chemical analyte;

measuring a response based on the reaction of the chemical analyte and the metal particle 5; and detecting the chemical analyte based on the measured response.

* * * * *